US008858476B2

(12) United States Patent
Ferenc et al.

(10) Patent No.: US 8,858,476 B2
(45) Date of Patent: Oct. 14, 2014

(54) PROTECTIVE CAST COVER FOR BATHING

(75) Inventors: Cser Ferenc, Kaposvar (HU); Laszlo Nagy, Boynton Beach, FL (US)

(73) Assignee: Laszlo Nagy, Boynton Beach, FL (US)

( * ) Notice: Subject to any disclaimer, the term of this patent is extended or adjusted under 35 U.S.C. 154(b) by 0 days.

(21) Appl. No.: 13/541,227

(22) Filed: Jul. 3, 2012

(65) Prior Publication Data

US 2012/0323153 A1 Dec. 20, 2012

Related U.S. Application Data

(63) Continuation-in-part of application No. 12/459,325, filed on Jun. 29, 2009, now abandoned.

(51) Int. Cl.
*A61F 5/00* (2006.01)
*A61F 13/04* (2006.01)

(52) U.S. Cl.
CPC .................................. *A61F 13/041* (2013.01)
USPC ........ 602/3; 602/20; 602/21; 602/23; 602/69; 602/78; 2/16; 2/22; 2/59; 2/159

(58) Field of Classification Search
USPC ......... 128/82; 602/3, 20, 21, 23, 69, 78; 2/16, 2/22, 59, 159
See application file for complete search history.

(56) References Cited

U.S. PATENT DOCUMENTS

| 2,244,871 | A | * | 6/1941 | Guinzburg | 2/59 |
| 4,178,924 | A | * | 12/1979 | Baxter | 602/3 |
| 4,422,454 | A | * | 12/1983 | English | 128/870 |
| 6,126,621 | A | * | 10/2000 | Aceves | 602/3 |
| 2006/0287623 | A1 | * | 12/2006 | Beck et al. | 602/3 |

OTHER PUBLICATIONS

"DuPont Tyvek—Uses and Applications"; www2.dupont.com/Tyvek (Dec. 26, 2007); accessed from http://web.archive.org May 16, 2013.*

* cited by examiner

*Primary Examiner* — Patricia Bianco
*Assistant Examiner* — Caitlin Carreiro
(74) *Attorney, Agent, or Firm* — Robert M. Downey, P.A.

(57) ABSTRACT

A cover adapted to be worn over a user's limb to shield a cast from water exposure includes a shell formed of a single layer of a flexible, water resistant and breathable material. The shell surrounds an interior of the cover, including a lower interior chamber and an upper interior chamber. An open top end communicates with the upper interior chamber and is sized to permit passage of the user's limb and the cast therethrough and into the upper and lower interior chambers. A cinch strap with a releasable securing mechanism closes the open top end around the user's limb. An inner cuff separating the interior chambers includes an elastomeric opening that fits snug against the user's limb, above the cast, and can be tightened using a secondary cinch strap and cooperating fasteners. A segment of water absorbing fabric on an interior surface for absorbing moisture and water.

6 Claims, 5 Drawing Sheets

PROTECTIVE CAST COVER FOR BATHING

This application is a continuation-in-part application of co-pending patent application Ser. No. 12/459,325, filed on Jun. 29, 2009.

BACKGROUND OF THE INVENTION

1. Field of the Invention

The present invention relates to protective covers for bandages and casts and, more particularly, to a cover device that fits over a person's hand or foot and at least a portion of the length of the person's arm or leg to protectively cover the bandage or cast.

2. Discussion of the Related Art

When a person is fitted with a bandage or cast for healing a wound or fractured bone, it is important to keep the bandage or cast dry in order to prevent infection, as well as to avoid deterioration of the bandage or cast. However, this can be difficult, especially when attempting to bathe in a tub or shower. Exposure of a bandage or cast to moisture is also a threat when it rains or if the person is engaged in an activity, such as boating, which presents the possibility of getting wet.

In order to provide protection against water exposure, others have proposed various sleeves, bags and cover devices that fit over a portion of the body and a bandage or a cast worn on that body portion. These various protective devices in the related art are typically formed of a plastic material that provides a water resistant barrier.

Typically, the protective cast covers in the related art are secured to the user's body with the use of an elastic band or tape. This means of closing the protective cover over the bandage or cast has been found to be inadequate in preventing entry of water or moisture into the protective cover. Moreover, the water resistant material of these protective cover devices, while effective to prevent penetration of water therethrough, fail to allow for air flow or breathing between the interior and exterior of the cover. This traps body heat which causes a rapid temperature rise within the interior of the cover device, resulting in excess perspiration and high humidity that remains contained inside the cover device. Perspiration and moisture that enters the cover device, as a result of the inadequate closure means, combined with the trapped hot, moist air within the cover can lead to foul odors, rash, fungus, infection and deterioration of the bandage or cast.

Accordingly, there remains a need for a protective device that can be easily fitted over a portion of a person's body to cover a bandage or cast, and wherein the device is adapted to be effectively sealed to prevent entry of water or moisture. There is a further need for a protective cover device that allows for breathing to prevent trapped heat and excessive perspiration within the inner chamber of the protective cover device.

Objects and Advantages of the Invention

Considering the foregoing, it is a primary object of the present invention to provide a protective cover that fits over a portion of a person's body to cover a bandage or cast, and wherein the protective cover device is adapted to close against the user's body in a manner that prevents entry of water or moisture under the cover device.

It is a further object of the present invention to provide a protective cover device which is adapted to fit over a hand or foot and at least partially over a person's arm or leg, and wherein the protective cover device includes a first closure mechanism providing a first barrier against water entry and a second closure mechanism providing a second barrier against water and moisture entry, and a moisture absorbent cuff providing a third barrier against water and moisture entry, thereby substantially minimizing the possibility of exposing the bandage or cast to water or moisture.

It is still a further object of the present invention to provide a protective cover device for covering a bandage or cast on a person's body, and wherein the protective cover device is made at least partially of a breathable material that allows for passage of air between an interior of the device and an exterior of the device while preventing transfer of moisture therethrough.

It is still a further object of the present invention to provide a protective cover device for covering a portion of a person's body and a bandage or cast worn on the person's body, and wherein the protective cover device is adapted to be adjustably closed against the person's body at multiple locations to thereby provide several barriers against entry of moisture or water.

It is still a further object of the present invention to provide a protective cover device that is adapted to be adjustably fitted over a portion of a person's body to cover a bandage or cast, and wherein the protective cover device is constructed as a single layer of water resistant and breathable material to protect against development of foul odors, rashes, fungus, infection and deterioration of the bandage or cast that can result from trapped heat and prolonged exposure to moisture or water.

These and other objects and advantages of the present invention are more readily apparent with reference to the following detailed description and accompanying drawings.

SUMMARY OF THE INVENTION

The present invention is directed to a protective cover device that is adapted to be worn over a user's limb to shield a bandage, wound dressing or cast from exposure to water and moisture. The protective cover is generally in the form of an elongate bag that has a shell formed of a single layer of flexible, water resistant and breathable material that allows for air flow communication between an interior of the elongate bag and an exterior atmosphere surrounding the protective cover device. In a preferred embodiment, the water resistant and breathable material is a flashspun high-density polyethylene fibrous material. The shell surrounds an interior that is sized and configured to comfortably receive a person's limb (i.e., hand and arm or foot and leg) as well as a bandage or cast that is worn on the person's limb. The interior of the cover device is divided between a lower interior chamber and an upper interior chamber. An open top end communicates with the upper interior chamber and is sized and configured to permit passage of the user's limb and the cast, bandage or dressing therethrough and into the upper and lower interior chambers. The open top end is closed snugly around the user's limb with the use of a cinch strap. The cinch strap is provided with releasable securing means for closing the open top end snug around the user's limb in order to provide a first barrier against water entry into the interior of the cover device. An inner cuff separates the upper and lower interior chambers. The inner cuff is secured to an inner surface of the shell of the cover device and surrounds a central opening that is fitted with an elastic band. The central opening of the cuff is adapted to permit passage of the user's hand or foot therethrough, as well as a portion of the limb and the bandage or cast, so that the bandage or cast is contained within the lower interior chamber. The elastic band fits snug against the user's limb, above the bandage or cast, and can be tightened using a secondary cinch strap and hook and loop fasteners fitted about the inner cuff to provide a second barrier against water entry into the lower interior chamber. The inner cuff also includes a water absorbing fabric on its interior surface for absorbing liquid or moisture that might get through the cuff opening, thereby providing a third barrier against moisture entry into the lower interior chamber.

BRIEF DESCRIPTION OF THE DRAWINGS

For a fuller understanding of the nature of the present invention, reference should be made to the following detailed description taken in conjunction with the accompanying drawings in which.

Like reference numerals refer to like parts throughout the several views of the drawings.

DETAILED DESCRIPTION OF THE PREFERRED EMBODIMENTS

Figure 1:
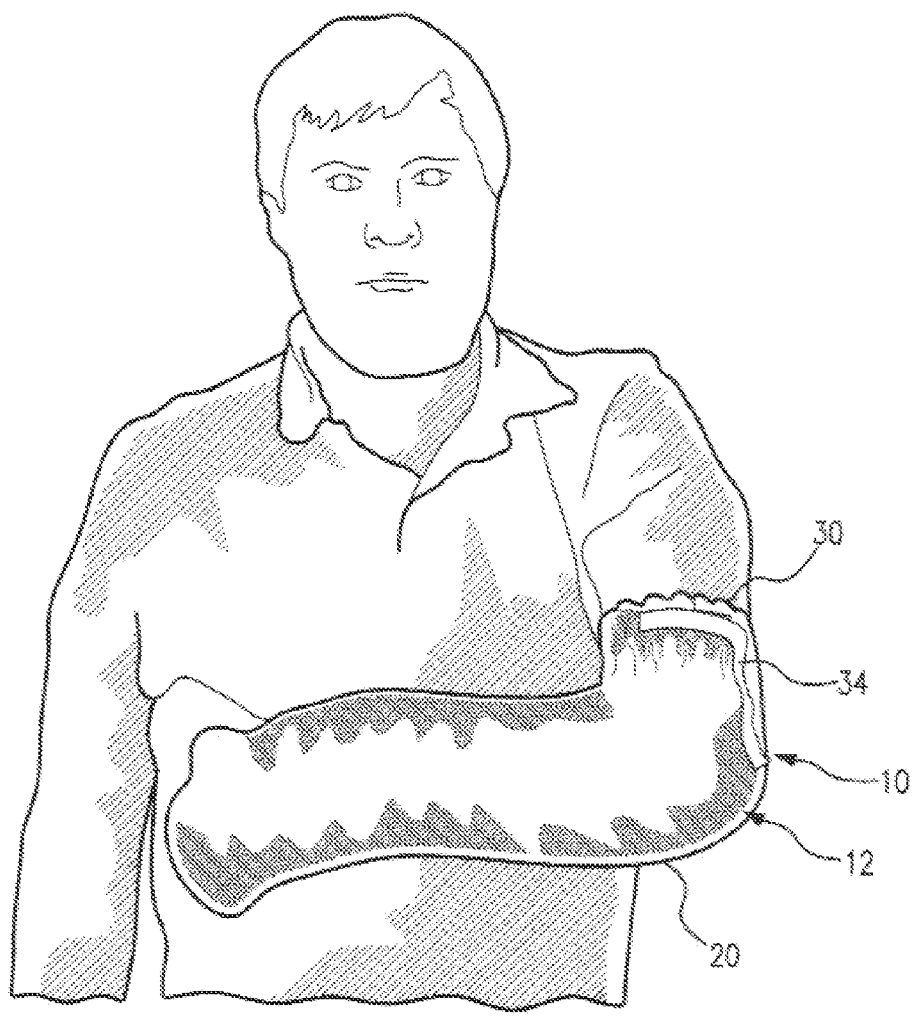
FIG. 1 is a front perspective view showing the protective cover device of the present invention fitted over the hand and arm of a person wearing a cast on their hand, wrist and forearm.

Referring to the several views of the drawings, the protective cover of the present invention is shown and is generally indicated as 10. The protective cover 10 is specifically adapted to be worn over a person's limb 51 to shield a cast from exposure to water and moisture. For the purposes of this application, the term "cast" further includes the terms "bandage and "wound dressing." The cast cover 10 includes a main body 12 formed and configured to cover a specific area of the body, such as a hand and at least a portion of an arm, as shown in FIGS. 1 and 3, or a foot and at least a portion of a leg, as shown in FIG. 4.

The main body of the cover device has a shell 20 that defines the overall size and shape of the cover device. The shell 20, forming the main body 12, has an open top end 30 communicating with an interior 40 that is surrounded by the shell. The shell 20 is formed of a single layer of a flexible, water resistant and breathable material that allows for air flow communication between the interior 40 and an exterior atmosphere surrounding the cover device 10. In a preferred embodiment, the water resistant and breathable material is a flashspun high-density polyethylene fibrous material. The interior 40 of the cover device includes an upper interior chamber 42 and a lower interior chamber 44. The open top end 30 communicates with the upper interior chamber 42 and is sized and configured to permit passage of a person's limb and a cast 50 therethrough and into the upper 42 and lower 44 interior chambers. The lower interior chamber 44 may be formed to generally conform to the shape of a hand, foot or other body part and is sufficiently sized to accommodate a cast 50 that is worn on the person's hand and arm or foot and leg.

Figure 2:
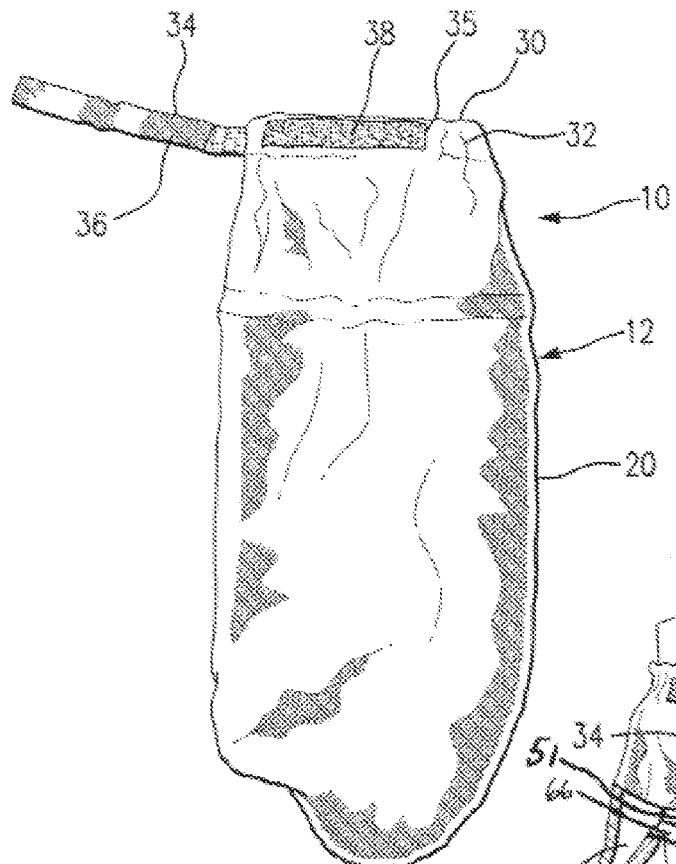
FIG. 2 is a front elevational view of the protective cover device.
Figure 3:
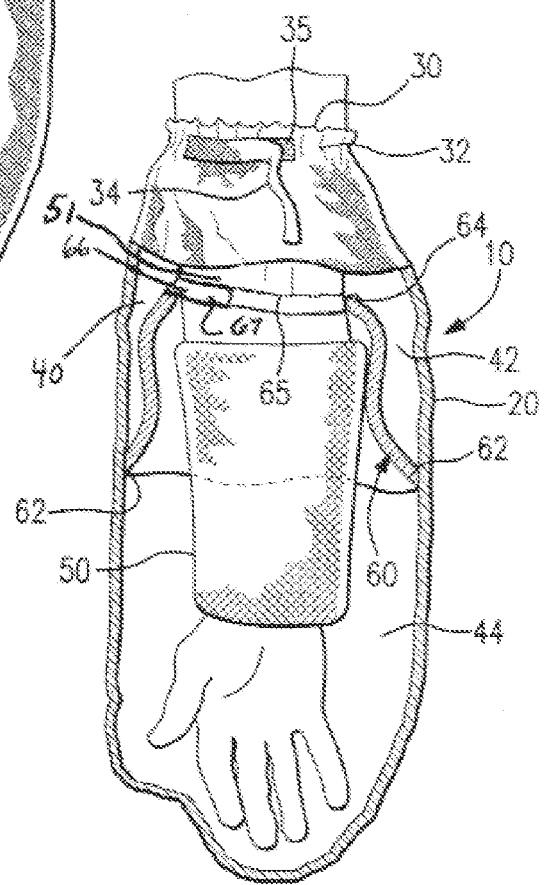
FIG. 3 is an elevational view, in partial cross-section, showing the protective cover device of the present invention fitted over the hand and forearm of a user to cover a cast or bandage worn on the user's wrist and lower forearm.
Figure 4:
FIG. 4 is a perspective view showing the protective cover device of the present invention worn over a user's foot and lower leg to cover a cast worn on the foot and lower leg.

Once the cover device 10 is pulled over the person's limb, to cover the cast 50, as seen in FIGS. 1, 3 and 4, the open top end 30 is closed against the person's limb to discourage entry of water into the interior 40 of the cover device. In a first embodiment, as shown in FIGS. 1-3, the open top end 30 is fitted with an elastic band 32 within the shell material to partially close the open top end when in a relaxed state. The elastic band 32 can be stretched to enlarge the open top end to allow insertion and removal of the person's hand, or foot and limb therethrough. The embodiment shown in FIGS. 1-3 further includes a cinch strap 34 having a first end 35 permanently attached to the shell 20 of the cover device 10. An inner face of the cinch strap 34 is fitted with one component 36 of a hook and loop fastener on a free end segment and is adapted for releasable engagement with a corresponding component 38 of a hook and loop fastener on an opposite end segment of the strap, adjacent the open top end 30. When the cover device 10 is worn on the user, as seen in FIG. 3, the cinch strap 34 is pulled to close the top end 30 snug against the person's limb 51, above the cast 50 and is held secured by the mating attachment of the hook and loop fasteners 36, 38. This provides a first barrier against entry of water into the interior 40 of the cover device 10.

The cover device further includes an interior annular cuff 60 that separates the upper 42 and lower 44 interior chambers. The cuff 60 is secured about its outer periphery 62 to an inner side of the shell. The cuff 60 includes a central opening 64, surrounded by an elastic band 65, that allows passage of the person's hand or foot, and a portion of the arm or leg, therethrough and into the lower interior chamber 44, as seen in FIG. 3, and is held secured by a secondary cinch strap 67 and mating attachment of hook and loop fasteners 66, 68. When properly worn, the elastic band 65 and hook and loop fasteners 66, 68 surrounding the central opening 64 of the cuff snugly engages the user's limb 51 above the cast 50, as shown in FIG. 3. This provides a second barrier against water entry into the lower interior chamber 44.

Figure 5:
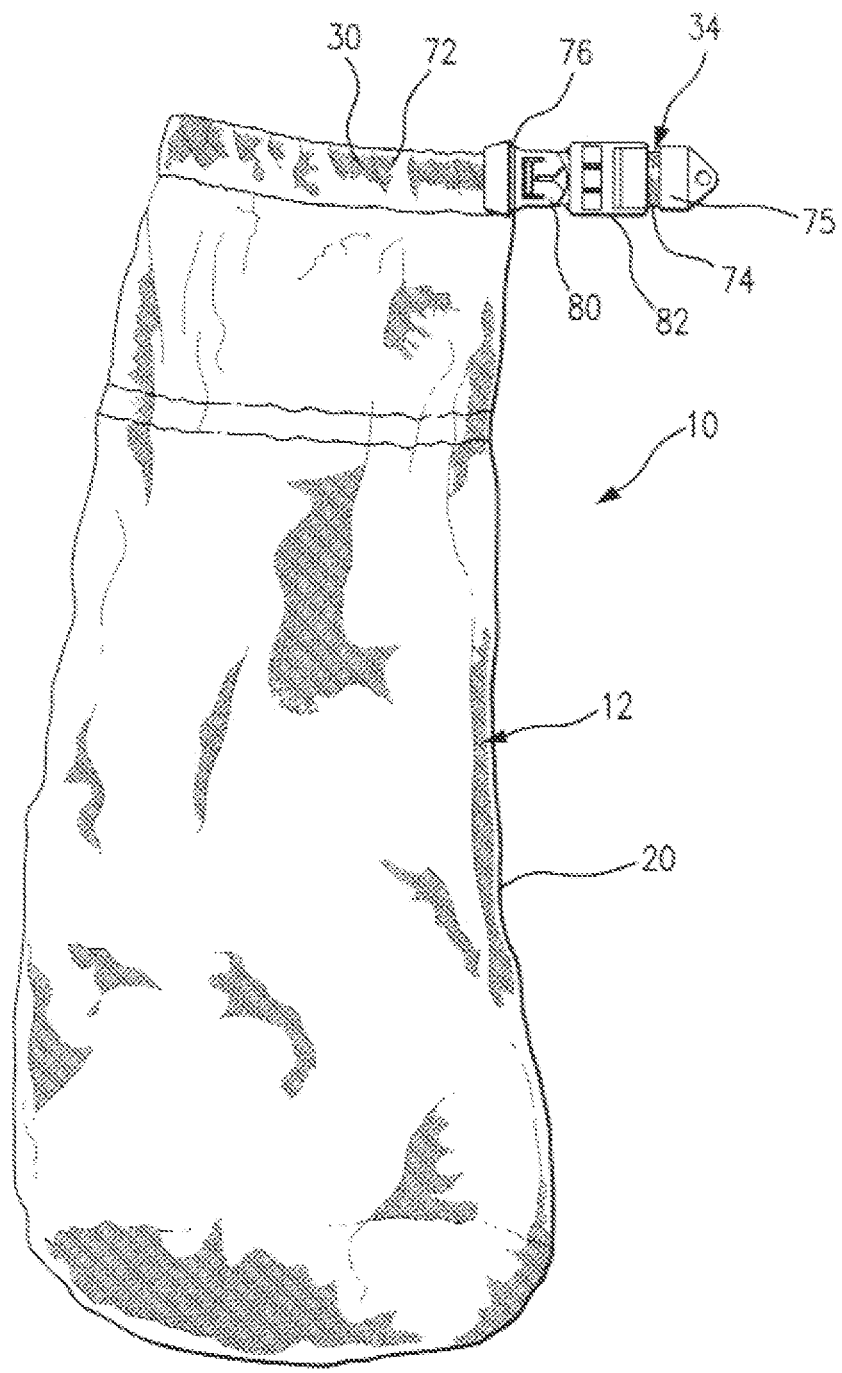
FIG. 5 is an elevational view of the protective cover device showing another embodiment of the strap securing mechanism on the upper end of the cover device.
Figure 6:
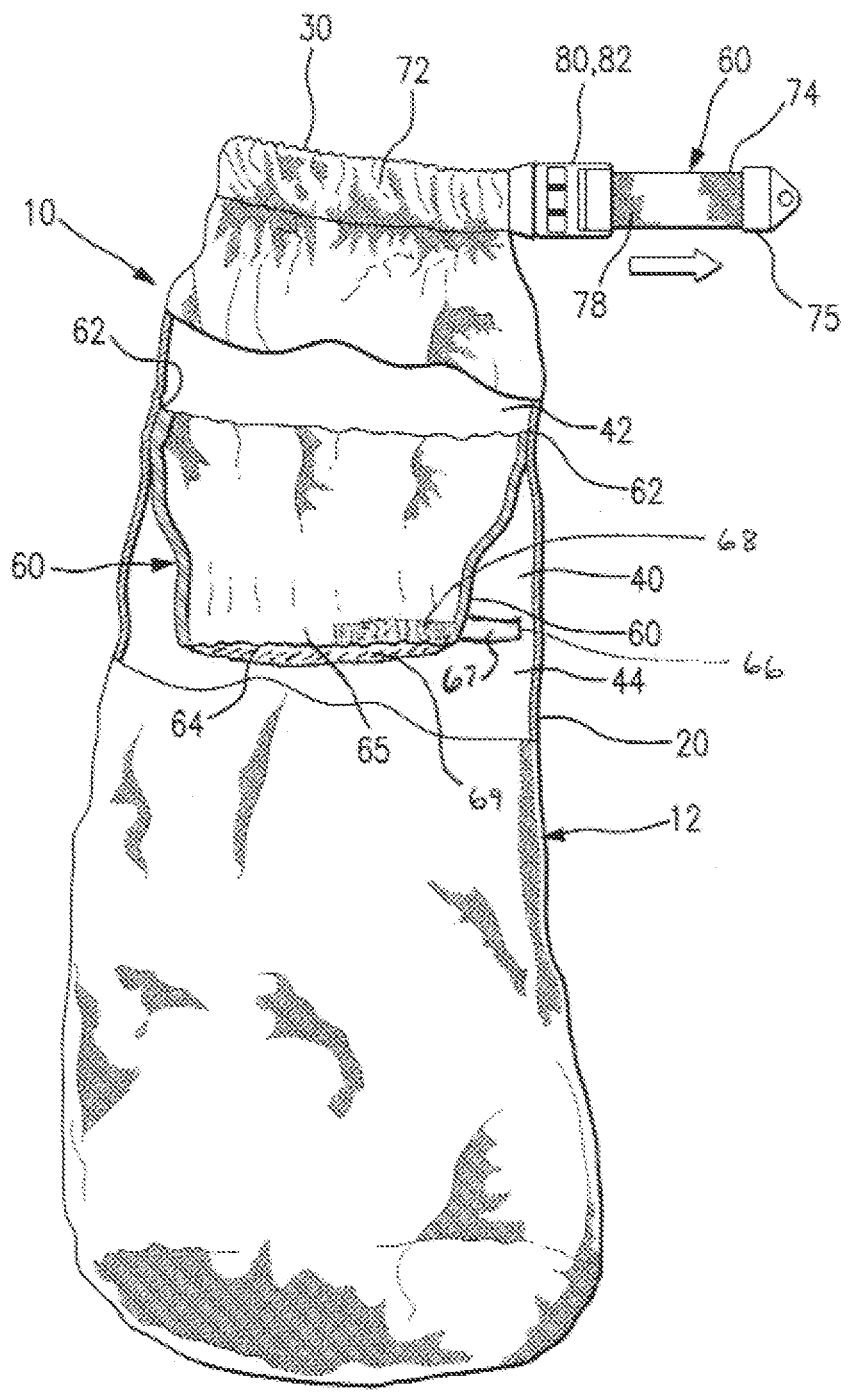
FIG. 6 is an elevational view, in partial cross-section, showing the protective cover device of FIG. 5 and illustrating movement of the cinch strap relative to a securing buckle in order to adjustably close the open top end of the cover device, and further showing a second cinch strap about the inner cuff opening.

FIGS. 4-6 illustrate a second embodiment of the cinch strap 70. In this particular embodiment, the cinch strap 70 extends through a channel 72 surrounding the open top end 30. Opposite ends of the cinch strap 70 remain exterior of the channel including a first end 74 fitted with a stop member 75 and an opposite end 76 fitted with a male component 80 of a buckle. A female component 82 of the buckle is slideably captivated on a first end zone 78 of the cinch strap 70 between the stop member 75 and the channel 72 surrounding the open top end. To close the top end 30 snug about the limb 51 of the user, the female component 82 of the buckle is secured to the male component 80 and, next, the first end 74 of the cinch strap 70 is pulled, as indicated by the directional arrow in FIG. 6, to partially close the open top end 30 until it is snug about the user's limb 51.

Further illustrated in FIGS. 3 and 6 is an integrally attached segment of liquid absorbing fabric 69, such as terrycloth, surrounding the interior surface of the cuff 60. When the cuff 60 is properly secured using the hook and loop fasteners 66, 68, the liquid absorbing fabric is held snugly against the user's limb 51, and absorbs any liquid that might enter beyond the first and second barriers. The liquid absorbing fabric 69 provides a third barrier against water entry into the lower interior chamber 44.

In a preferred embodiment, both the shell 20 and the interior annular cuff 60 are formed of a material made of flashspun high-density polyethylene fibers, which is a water resistant, breathable material. An example of a water resistant and breathable material that is suitable for manufacture of the cover device, and particularly the shell and interior cuff, is TYVEK® from the DuPont company, a flashspun high-density polyethylene fibrous material.

While the present invention has been shown and described in accordance with several preferred and practical embodiments, it is recognized that departures from the instant disclosure and fully contemplated within the spirit and scope of the present invention which is not to be limited except as defined in the following claims as interpreted under the Doctrine of Equivalence.

What is claimed is:

1. A protective cover device for covering a sensitive area on a limb of a user when bathing, said cover device comprising:

an elongate shell including an outer surface, an inner surface, a closed bottom, a closed side wall structure surrounding an interior of said elongate shell and including an upper interior chamber and a lower interior chamber, and an open top end communicating with said upper interior chamber, and wherein said elongate shell is formed of a single layer of a flexible, water resistant and breathable material that allows air flow communication between said interior of said elongate shell and an exterior atmosphere surrounding said cover device;

a first barrier for discouraging entry of water and moisture into the lower interior chamber, and said first barrier being defined by a cinch strap extending through a channel surrounding the open top end of said elongate shell and being structured and disposed for tightening the open top end against the user's limb above the sensitive area;

an interior annular cuff contained entirely within the interior of said elongate shell and including an outer periphery and an opposite free distal end surrounding a central opening, and said interior annular cuff being secured about its outer periphery to said inner surface of said elongate shell between the upper interior chamber and the lower interior chamber and extending freely and loosely therefrom to the central opening at said free distal end, and the central opening being surrounded by a second cinch strap having a first component of a hook and loop fastener structured and disposed for releasable, mating attachment to a second component of a hook and loop fastener on the free distal end of said interior annular cuff throughout a range of attached positions for adjusting the size of the central opening and tightening the central opening of said interior annular cuff against the user's limb above the sensitive area and defining a second barrier between the first barrier and the lower interior chamber for discouraging entry of water and moisture into the lower interior chamber, and said interior annular cuff being formed of a water resistant and breathable material that allows air flow communication between the upper and lower interior chambers; and a third barrier for discouraging entry of water and moisture into the lower interior chamber, and said third barrier being defined by a liquid absorbing fabric strip on an inner facing surface of said interior annular cuff, adjacent to the free distal end, for direct contact with the user's limb above the sensitive area, and said liquid absorbing fabric strip being structured and disposed for absorbing liquid that passes beyond the first barrier and the second barrier.

2. The protective cover device as recited in claim 1 wherein said cinch strap includes opposite end segments that remain exterior of said channel including a first end segment, a second end segment, and a releasable securing mechanism on said opposite end segments for holding the open top end sealed against the user's limb.

3. The protective cover device as recited in claim 2 wherein said releasable securing mechanism comprises:

a female component of a releasable buckle on said first end segment of said cinch strap; and a male component of the releasable buckle on said second end segment of said cinch strap for releasable, interlocked attachment with said female component.

4. The protective cover device as recited in claim 3 wherein said female component is structured to slide along said first end segment of said cinch strap, and said device further comprising a stop member on a distal end segment of said cinch strap for limiting movement of said female component.

5. The protective cover device as recited in claim 1 wherein the single layer of the flexible, water resistant and breathable material forming said elongate shell is a flashspun high-density polyethylene fibrous material.

6. The protective cover device as recited in claim 1 wherein the water resistant and breathable material forming said interior annular cuff is a flashspun high-density polyethylene fibrous material.

* * * * *